United States Patent

Kurono et al.

[11] Patent Number: 4,871,740
[45] Date of Patent: Oct. 3, 1989

[54] GLYCYRRHETIC ACID DERIVATIVES AND USE THEREOF

[75] Inventors: Masayasu Kurono, Mie; Ryoichi Unno, Nagoya; Hiromoto Kimura; Mitsuru Oka, both of Kasugai; Keiko Hasegawa, Inazawa; Shinichi Ikeda; Noboru Kuboyama, both of Kasugai; Takashi Ito, Gifu; Kiichi Sawai, Funabashi; Shunshuke Ito, Hiroshima, all of Japan

[73] Assignee: Sanwa Kagaku Kenkyusho Co., Ltd., Nagoya, Japan

[21] Appl. No.: 124,518

[22] Filed: Nov. 24, 1987

[30] Foreign Application Priority Data

Nov. 28, 1986 [JP] Japan ............................. 61-281975

[51] Int. Cl.⁴ .................. A61K 31/495; C07D 241/04
[52] U.S. Cl. .................... 514/255; 544/380; 558/429; 560/115; 560/116; 560/159; 560/162; 562/490; 564/188; 514/519; 514/529; 514/557; 514/563; 514/564; 514/616; 514/622
[58] Field of Search ............ 544/380; 558/429; 560/115, 116, 159, 162; 562/498; 564/188; 514/255, 519, 529, 557, 563, 564, 616, 623

[56] References Cited

U.S. PATENT DOCUMENTS 3,070,623 12/1962 Gottfried et al. .................. 560/115
3,070,624 12/1962 Baxendale et al. ................. 560/115

FOREIGN PATENT DOCUMENTS 753773 7/1970 Belgium .
32798 2/1969 Japan .
1346871 2/1974 United Kingdom .

*Primary Examiner*—Richard L. Raymond
*Assistant Examiner*—James H. Turnipseed
*Attorney, Agent, or Firm*—Armstrong, Nikaido, Marmelstein, Kubovcik & Murray

[57] ABSTRACT

A glycyrrhetic acid derivative of the formula $$A_2-(CH_2)_m-(CH=CH)_n-A_1- \quad (I)$$

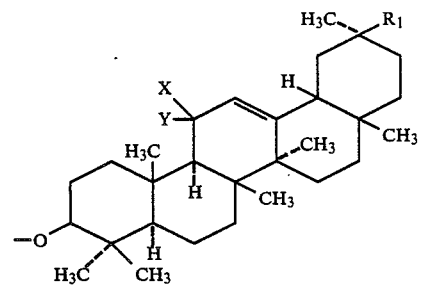

wherein X and Y are hydrogen atom, respectively or X is oxygen atom together with Y, $A_1$ is methylene or carbonyl radical, $A_2$ is hydrogen atom, cyano, carbamoyl, carboxyl radical or alkoxycarbonyl group, m and n are an integer, respectively, $R_1$ is a radical of $$-COOR_2 \quad (Ia)$$

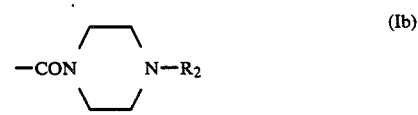

or $$-CONH-(CH_2)_l-A_3-R_2 \quad (Ic)$$

in which $R_2$ is an alkyl, alkenyl group, phenyl radical or a substituted phenyl radical, $A_3$ is S, O or NH, and l is an integer, a process for the preparation of the derivatives, and use of the derivative as a pharmaceutical agent.

18 Claims, No Drawings

GLYCYRRHETIC ACID DERIVATIVES AND USE THEREOF

BACKGROUND OF THE INVENTION

1. Field of the Invention

The present invention relates to novel glycyrrthetic acid derivatives, a process for the preparation thereof as well as an antiulcer agent comprising at least one of the derivatives, as an effective ingredient.

2. Related Arts

It has been known that glycyrrhetic acid and certain derivatives thereof have various pharmacological activities such as antidigestive ulcer, antiinflammatory, antiallergic and the like actions.

As compounds of this kind, for instance, following compounds have been proposed.

Carbenoxolone (U.S. Pat. No. 3070623);

Esters at 30-position of glycyrrhetic acid (U.S. Pat. No. 3070624);

Amine acid salt of glycyrrhetic acid (Jap. Examine Pat. Appln. Gazette No. 32798/1969);

Amides of Glycyrrhetic acid (Belgian Pat. No. 753773); and

Amides of 11-deoxoglycyrrhetic acid (BP 1346871).

The present inventors have proposed a novel synthetic method of 11-deoxoglycyrrhetic acid (Jap. Unexamined Pat. Appln. Gazette No. 70638/1984) and novel hemi-ester derivatives of 11-deoxoglycyrrhetic acid (Jap. Unexamined Pat. Appln. Gazette No. 8044/1983).

The glycyrrhetic acid and derivatives thereof have the useful pharmacological activities as referred to but show a disadvantage of that its administration shall cause an abnormality in electrolyte metabolism to bring a Na-accumulation and K-diuresis, an advanced stage of which results an appearance of a hypertension, hypocalcemia, edemia or the like symptom, so-called—Pseudoaldosteronism—.

Therefore, it is the actual circumstance that the use of glycyrrhetic acid or its derivative is highly restricted in dosage and giving period, in view of safety.

SUMMARY OF THE INVENTION

An object of the invention is to provide novel glycyrrhetic acid derivatives and salts thereof, which show a high antiulcer activity and are able to reduce side effects thereof, such as pseudoaldosteronism.

Another object of the invention is to provide a process for the preparation of such novel derivatives and salts.

A still other object of the invention is to provide a pharmaceutical composition which comprises at least one of such novel derivatives, as an effective ingredient.

According to the invention, the objects as referred to and other objects is apparent by fully understanding the invention can basically be attained by a glycyrrhetic acid derivative of the formula

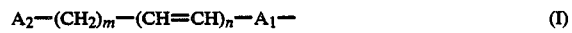

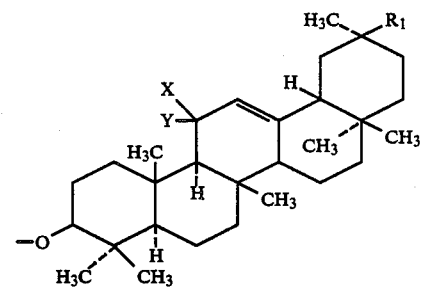

wherein X and Y are hydrogen atom. respectively or X is oxygen atom together with Y, $A_1$ is methylene or carbonyl radical, $A_2$ is hydrogen atom, cyano, carbamoyl, carboxy radical or alkoxycarbonyl group, m and n are an integer, respectively, $R_1$ is a radical of

or

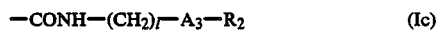

in which $R_2$ is an alkyl, alkenyl group, phenyl radical or a substituted phenyl radical, $A_3$ is S, O or NH, and l is an integer.

In the definition of substituents in Formula I, the alkyl group may be of straight-chain alkyl radicals, branched-chain alkyl radicals or cycloalkyl radicals. As examples for the straight-chain alkyl radicals, one having 1 to 10 carbon atoms, for instance methyl, ethyl, n-propyl, n-butyl, n-pentyl, n-hexyl, n-decyl and the like may be listed. As the branched-chain alkyl radicals, isopropyl, isobutyl, sec-butyl, tert-butyl, isopentyl and the like may be listed. As the cycloalkyl radicals, cyclopropy, cyclobutyl, cylopentyl, cyclohexyl and the like may be listed. As the alkenyl radicals, terpenic hydrocarbon residues, for instance a group of

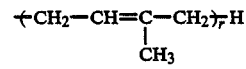

wherein r is an integer of 1 to 10, phytyl and the like may be listed. As the substituents for the substituted phenyl group, methoxy, halogen atom, hydroxy, nitro and the like may be listed.

According to the invention, the glycyrrhetic acid derivatives (I) can be prepared, in accordance with any one of following synthetic routes.

Route A

-continued
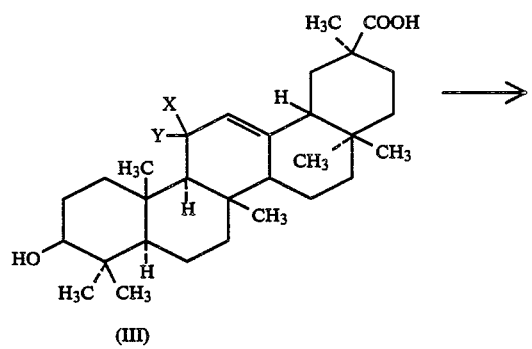
(III)
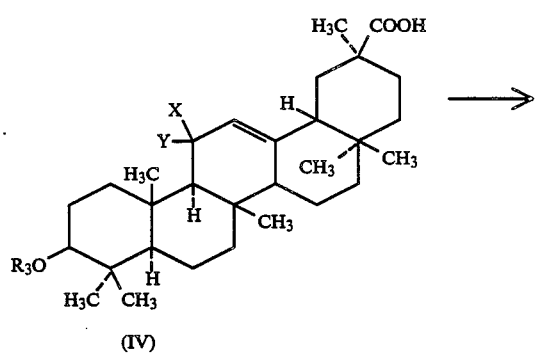
(IV)
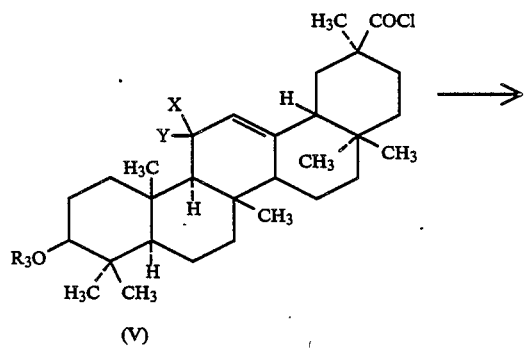
(V)
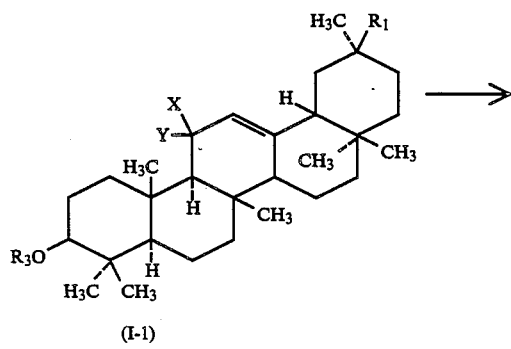
(I-1)

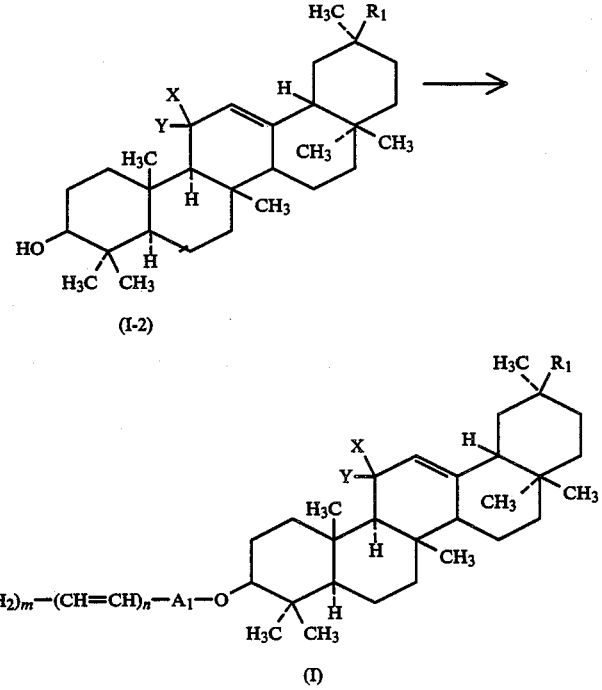

(I-2)

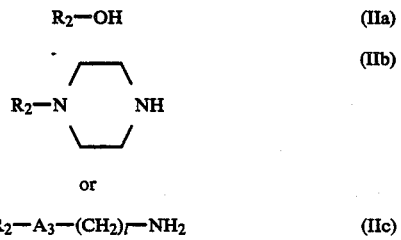

(I)

In the above formulae, X, Y, $A_1$, $A_2$, $R_1$, m and n have the meanings as referred to, and $R_3$ is a protective radical for hydroxy radical.

According to this synthetic route, the hydroxy radical of compound (III) is firstly protected in a conventional manner to prepare the compound (IV). As the protective radical, any of them capable to protect the hydroxy radical may be employed but it is preferable to select acetyl, trifluoroacetyl, trimethylsilyl or the like. In the next place, the compound (IV) is reacted with a halogenating agent to convert into the compound (V). As the halogenating agent, thionyl chloride, phosphorous oxychloride or the like is preferable. Please note that among the compounds employed for such steps, the compound (III) of 11-deoxoglycyrrhetic acid has been known and can be prepared in accordance with the disclosures as given by Ruzicka et al "Helv. Chim. Acta" Vol. 20, pages 1271 (1973) or in Jap. Unexamined Pat. Appln. Gazette No. 70638/1984. Further, the compounds (IV) and (V) with acetyl radical as protective one have also been known and in these cases, the compounds can be prepared in accordance with the disclosure given by Corey et al "J. Am. Chem. Soc." Vol. 81, pages 1745 (1959) and Ruzicka et al "Helv. Chim. Acta" Vol. 22, pages 195 (1939), respectively.

The compound (V) is then reacted with a compound of the formula $R_2$—OH  (IIa)

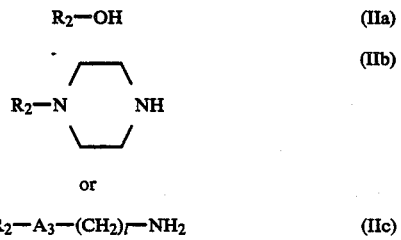

or $R_2$—$A_3$—$(CH_2)_l$—$NH_2$  (IIc)

wherein $R_2$, $A_3$ and l have the meanings as referred to, in a suitable solvent, for instancse methylene chloride, chloroform or the like and in the presence of a tertiary amine at a temperature of 0° to 40° C. to prepare the compound (I-1). The protective radical in the compound (I-1) can selectively be removed to prepare the comound (I-2) by treating same at 0° to 40° C. in a suitable solvent such as methanol, ethanol, tetrahydrofuran, 1,4-dioxane or the like and in the presence of a basic catalyst such as sodium hydroxide, potassium hydroxide, potassium carbonate and the like or a acidic catalyst such as a mineral acid or organic acid. The desired compound (I) can be prepared by reacting the compound (I-2) with a compound of the formula

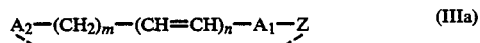  (IIIa)

or $A_2$—$(CH_2)_m$—$(CH=CH)_n$—$A_1$  (IIIb)

wherein $A_1$, $A_2$, m and n have the meanings as referred to, and Z is a halogen atom or diazo radical, or an acid anhydride residue together with $R_1$ and $R_2$.

In case of that the compound (IIIa) is the acid halogenide or acid anhydride, the reaction proceeds in a suitable solvent such as methylene chloride, toluene, xylene, pyridine and the like or in the absence of the solvent, in the presence or absence of a tertiary amine and at a temperature of 0° C. to a boiling temperature of the solvent. In case of that the compound (IIIa) is the diazo-compound while, the reaction proceeds smoothly in a suitable solvent such as methylene chloride, in the presence of a rhodium catalyst such as rhodium tetraacetate and at a temperature of 0° to 40° C.

Route B

III + IIIb

-continued
Route B

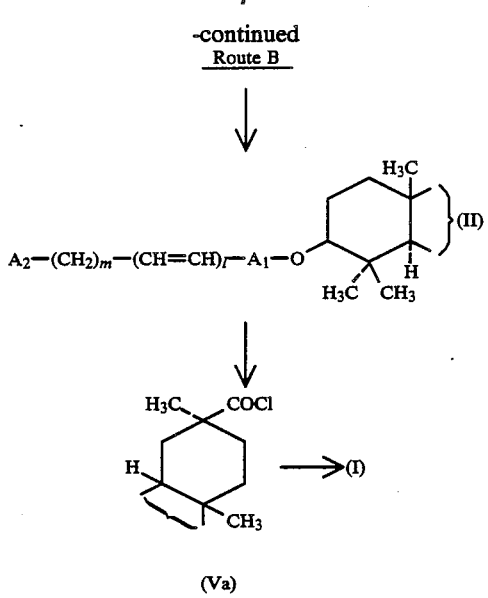

wherein $A_1$, $A_2$, l and m have the meanings as referred to.

This route utilizes the compound (II) which can be prepared by reacting the compounds (III) and (IIIb) in the Route A.

The reaction between the compounds (III) and (IIIb) proceeds smoothly in a suitable solvent such as tetrahydrofuran, 1,4-dioxane or the like, in the presence of a base such as sodium hydride, lithium hydride, sodium amide or the like, and at 0° C. to a boiling temperature of the solvent.

By treating the carboxyl radical in the compound (II) with a halogenating agent as in the Route A, the compound (II) can be converted into the compound (Va) which is converted into the desired compound (I) by reacting same with the compound (IIa), (IIb) or (IIc) as in the Route A.

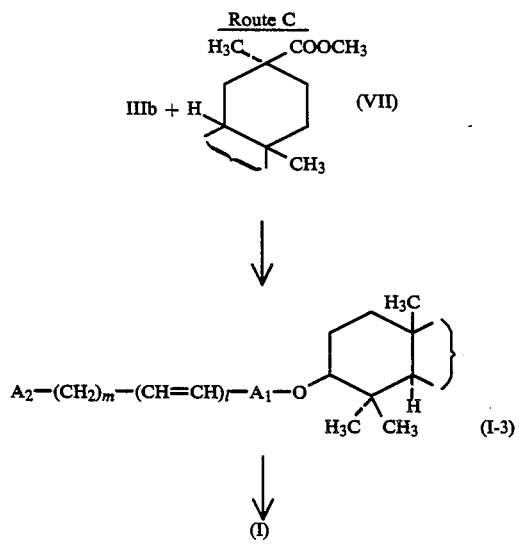

The compound (VII) to be employed for this Route has been known and can be prepared by starting from the compound (III) and in accordance with the disclosure as given by Corey et al "J. Am. Chem. Soc." Vol. 81, page 1745 (1959), which compound is reacted with the compound (IIIb) referred to in the Route A.

The resulting compound (I-3) can be converted into the desired compound (I) by hydrolizing the same in a solvent such as dimethylsulfoxide, ethanol or the like, in the presence of a basic catalyst such as sodium hydroxide, potassium hydroxide or the like and at a temperature of 0° C. to a boiling temperature of the solvent.

The compound (I) can be converted into its salt by reacting same in a solvent such as water, methanol, ethanol or the like with a base such as sodium hydroxide, potassium hydroxide, sodium carbonate, potassium carbonate, aluminum hydroxide or the like in an equivalent amount.

The compound (I) and/or salt thereof can be made into a drug. A formulation for the drug is carried out in a conventional manner to form a tablet, capsule, granule, powder or the like. A dosing amount of the compound or or salt for human depends on a kind of same, a symptom of patient, form of the drug and other factors but, in general, is selected in a range of 100 to 3000 mg/day for an adult.

PREFERRED EMBODIMENTS OF THE INVENTION

The invention will now be further explained with reference to Referece Examples, Manufacturing Examples, Pharmacological Test Examples and Examples for preparing a drug.

REFERENCE EXAMPLE 1

N-[2-(3,7-Dimethyl-2,6-octadien-1-ylthio)ethyl]-3β-acetoxy-18β-olean-12-en-30-amide (Compound 1a)

To a solution of 15.0 g (29.1 mmol) of 3β-acetoxy-18β-olean-12-en-30-oyl chloride and 2.94 g (29.1 mmol) of triethylamine in 200 ml of methylene chloride was added dropwise 6.20 g (29.1 mmol) of 2-(3,7-dimethyl-2,6-octadien-1-ylthio)ethylamine with stirring and then the mixture was stirred for 2 hours at 10° to 20° C.

The reaction mixture was washed with water. The organic layer was dried over sodium sulfate and concentrated in vacuo. The resulting residue was chromatographed on silica gel and eluted with methylene chloride to give 18.0 g (90.0%) of the desired compound (1a).

MS (EI/DI) m/z: 693 (M+), 79 (base peak).

REFERENCE EXAMPLE 2

3β-Acetyl-11-deoxoglycyrrhetic acid amides and ester (Compounds Ib–Ii) listed in the following Table 1 were prepared with use of the corresponding amines or alcohol and 3β-acetoxy-18β-olean-12-en-30-oyl chloride, by the similar procedure as in the case of Reference Example 1.

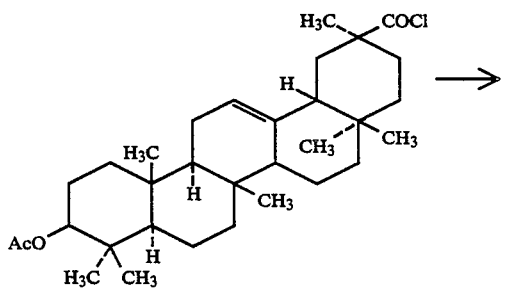

-continued

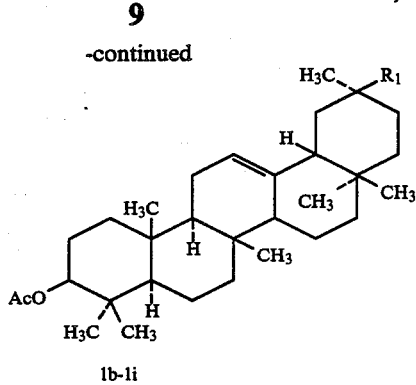

1b-1i stirring and then the mixture was stirred for 2 hours at 10° to 20° C.

The reaction mixture was washed with water. The organic layer was dried over sodium sulfate and concentrated in vacuo. The resulting residue was chromatographed on silica gel and eluted with methylene chloride to give 36.0 g (92.8%) of the desired compound (1j).

MS (EI/DI) m/z: 775 (M+), 572 (base peak).

REFERENCE EXAMPLE 4

3β-Acetylglycyrrhetic acid amides (Compounds 1k and 1l) listed in following Table 2 were prepared with use of the corresponding amines and 3β-acetoxy-11-oxo-18β-olean-12-en-30-oyl chloride, by the similar

TABLE 1

| Compd. | $R_1$ | Yield (%) | m.p. (°C.) | MS(EI/DI) (m/Z) |
|---|---|---|---|---|
| 1b | CONH–CH₂CH₂–S–(CH₂C(CH₃)=CHCH₂)₃–H | 96.5 | oil | 761 (M+) 453 (base peak) |
| 1c | CONH–CH₂CH₂–S–(CH₂C(CH₃)=CHCH₂)₄–H | 100 | oil | 829 (M+) 189 (base peak) |
| 1d | CONH–CH₂CH₂–S–(CH₂C(CH₃)=CHCH₂)₉–H | 97.1 | amorphous | 453 69 (base peak) |
| 1e | CONH–CH₂CH₂–S–(CH₂C(CH₃)=CHCH₂)₁₀–H | 100 | amorphous | 453 81 (base peak) |
| 1f | CONH–CH₂CH₂–S–CH₂C(CH₃)=CH(CH₂CH₂CH(CH₃)CH₂)₃–H | 100 | oil | 835 (M+) 556 (base peak) |
| 1g | CON(piperazine)N–(CH₂C(CH₃)=CHCH₂)₃–H | 100 | amorphous | 770 (M+) 69 (base peak) |
| 1h | COO–(CH₂C(CH₃)=CHCH₂)₃–H | 89.2 | 126–129 | 702 (M+) 69 (base peak) |
| 1i | CON(piperazine)N–(2-methoxyphenyl) | 98.6 | 210–212 | 672 (M+, base peak) |

REFERENCE EXAMPLE 3

N-[2-(3,7,11-Trimethyl-2,6,10-dodecatrien-1-ylthio)ethyl]-3β-acetoxy-11-oxo-18β-olean-12-en-30-amide (Compound 1j)

To a solution of 26.6 g (50.0 mmol) of 3β-acetoxy-11-oxo-18β-olean-12-en-30-oyl chloride and 5.06 g (50.0 mmol) of triethylamine in 400 ml of methylene chloride was added dropwise 14.1 g (50.0 mmol) of 2-(3,7,11-trimethyl-2,6,10-dodecatrien-1-ylthio)ethylamine with procedure as in the case of Reference Example 3.

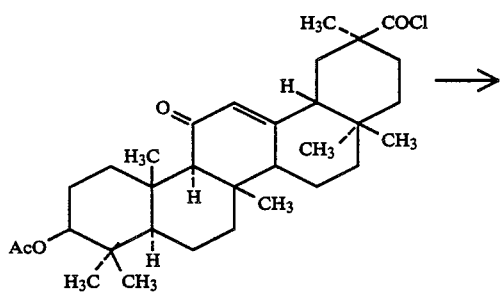

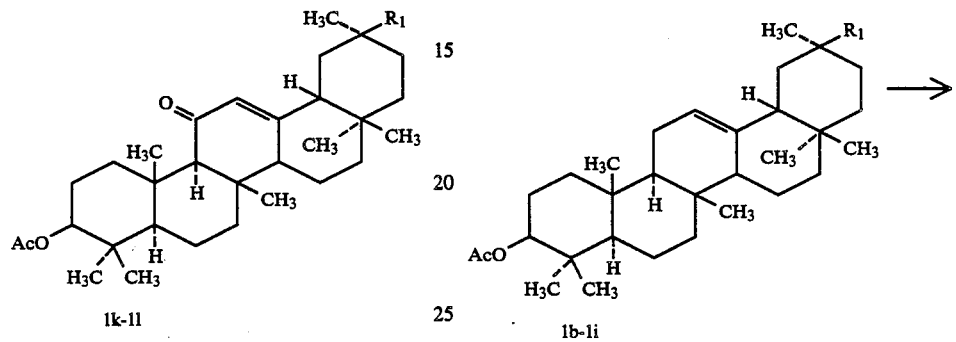

1k-1l                                      1b-1i residue was chromatographed on silica gel and eluted with 5% ethyl ether-methylene chloride to give 15.0 g (89.0%) of the desired compound (2a).

MS (EI/DI) m/z: 651 (M+), 69 (base peak).

REFERENCE EXAMPLE 6

$3\beta$-Hydroxy-$18\beta$-olean-12-en-30-amides and ester (Compounds 2b–2i) listed in following Table 3 were prepared with use of the corresponding $3\beta$-acetoxy-11-oxo-$18\beta$-olean-12-en-30-amides or ester (1b–1i), by the similar procedure as in the case of Reference Example 5.

TABLE 2

| Compd. | R₁ | Yield (%) | m.p. (°C.) | MS(EI/DI) (m/Z) |
|---|---|---|---|---|
| 1k | CONH-CH₂CH₂-S-(CH₂CH=C(CH₃)-)₁₀H | 91.6 | oil | 69 (base peak) |
| 1l | CON(piperazine)-N-C₆H₄-OMe (ortho) | 100 | amorphous | 686 (M+)<br>149 (base peak) |

REFERENCE EXAMPLE 5

N-[2-(3,7-Dimethyl-2,6-octadien-1-ylthio)ethyl]-$3\beta$-hydroxy-$18\beta$-olean-12-en-30-amide (Compound 2a)

To a solution of 18.0 g (26.0 mmol) of N-[2-(3,7-dimethyl-2,6-octadien-1-ylthio)ethyl]-$3\beta$-acetoxy-$18\beta$-olean-12-en-30-amide (Compound 1a obtained by Reference Example 1) in 100 ml of 1,4-dioxane was added 100 ml of 5% NaOH-MeOH and the resulting mixture was stirred for 5 hours at 20° C.

The reaction mixture was poured into ice water and extracted with chloroform (150 ml×2) and combined organic extracts were washed with water, dried over sodium sulfate and concentrated in vacuo. The resulting

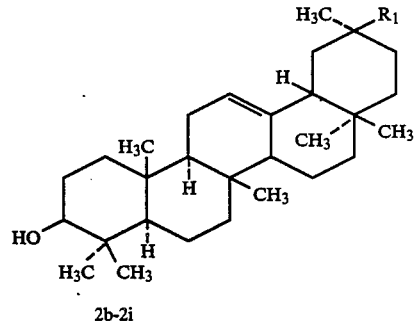

2b-2i

TABLE 3

| Compd. | R₁ | Yield (%) | m.p. (°C.) | MS(EI/DI) (m/Z) |
|---|---|---|---|---|
| 2b | CONH-CH₂CH₂-S-(CH₂CH=C(CH₃)-)₃H | 74.2 | amorphous | 720 (M+)<br>515 (base peak) |
| 2c | CONH-CH₂CH₂-S-(CH₂CH=C(CH₃)-)₄H | 94.1 | amorphous | 787 (M+)<br>189 (base peak) |

TABLE 3-continued

| Compd. | R₁ | Yield (%) | m.p. (°C.) | MS(EI/DI) (m/Z) |
|---|---|---|---|---|
| 2d | CONH-CH₂CH₂-S-(CH₂CH=C(CH₃)CH₂)₉-H | 76.6 | oil | 516, 69 (base peak) |
| 2e | CONH-CH₂CH₂-S-(CH₂CH=C(CH₃)CH₂)₁₀-H | 81.4 | oil | 683, 69 (base peak) |
| 2f | CONH-CH₂CH₂-S-CH₂CH=C(CH₃)(CH₂CH₂CH₂CH(CH₃))₃-H | 95.4 | amorphous | 793 (M+), 514 (base peak) |
| 2g | CON(piperazinyl)-N-(CH₂CH=C(CH₃)CH₂)₃-H | 98.7 | 102–105 | 728 (M+, base peak) |
| 2h | COO-(CH₂CH=C(CH₃)CH₂)₃-H | 100 | oil | 248 (base peak) |
| 2i | CON(piperazinyl)-N-(2-MeO-C₆H₄) | 81.0 | 219–220 | 630 (M+), 149 (base peak) |

REFERENCE EXAMPLE 7

N-[2-(3,7,11-Trimethyl-2,6,10-dodecatrien-1-ylthio)ethyl]-3β-hydroxy-11-oxo-18β-olean-12-en-30-amide (Compound 2j)

To a solution of 36.0 g (46.4 mmol) of N-[2-(3,7,11-trimethyl-2,6,10-dodecatrien-1-ylthio)ethyl]-3β-acetoxy-11-oxo-18β-olean-12-en-30-amide (Compound 1j obtained by Reference Example 3) in 360 ml of 1,4-dioxane was dded 360 ml of 5% NaOH-MeOH and the resulting mixture was stirred for 3 hours at 20° C.

The reaction mixture was poured into ice water and extracted with methylene chloride (500 ml×2) and combined organic extracts were washed with water, dried over sodium sulfate and concentrated in vacuo. The resulting residue was chromatographed on silica gel and eluted with 5% ethyl ether-methylene chloride to give 30.7 g (90.3%) of the desired compound (2j).

Melting point: 70°–75° C.

MS (EI/DI) m/z: 734 (M+), 531 (base peak).

REFERENCE EXAMPLE 8

3β-Hydroxy-11-oxo-18β-olean-12-en-30-amide derivatives (Compounds 2k and 2l) listed in following Table 4 were prepared with use of the corresponding 3β-acetoxy-11-oxo-18β-olean-12-en-30-amides (1k and 1l), by the similar procedure as in the case of Reference Example 7.

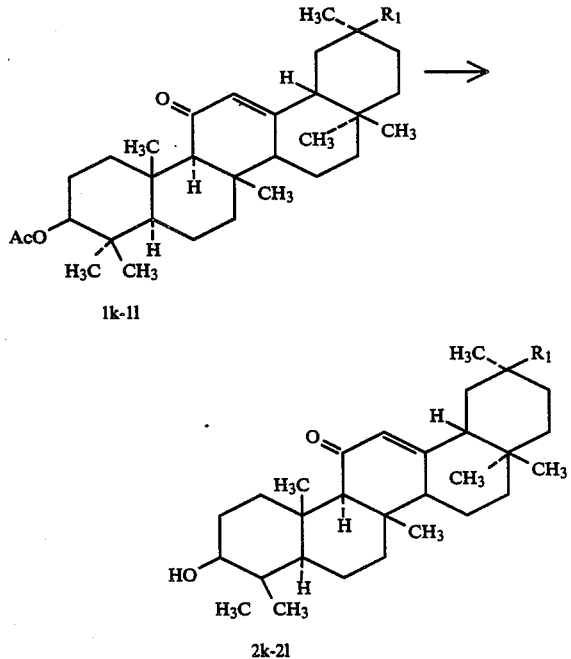

TABLE 4

| Compd. | R₁ | Yield (%) | m.p. (°C.) | MS(EI/DI) (m/z) |
|---|---|---|---|---|
| 2k | CONH-CH₂CH₂-S-(CH₂-CH=C(CH₃)-CH₂)₁₀-H | 84.1 | oil | 69 (Base peak) |
| 2l | CON(piperazinyl)-N-(2-methoxyphenyl) | 76.6 | 179–182 | 644 (M+) 149 (base peak) |

EXAMPLE 1

N-[2-(3,7-Dimethyl-2,6-octadien-1-ylthio)-ethyl]-3β-(3-carboxy-cis-propenoyloxy)-18β-olean-12-en-30-amide (Compound 3a)

A mixture of 12.0 g (18.4 mmol) of N-[2-(3,7-dimethyl-2,6-octadien-1-ylthio)ethyl]-3β-hydroxy-18β-olean-12-en-30-amide (Compound 2a obtained by Reference Example 5) and 36.0 g (0.368 mol) of maleic anhydride was heated at 100° C. for 2 hours with stirring and under argon atmosphere.

The reaction mixture was poured into 1 liter of water and extracted with ethyl ether (500 ml×2) and combined organic extracts were washed with water (1 liter×3). dried over sodium sulfate and concentrated in vacuo. The resulting residue was chromatographed on silica gel and eluted with methylene chloride-methanol (50:1) to give 7.00 g (51.0%) of the desired compound (3a).

MS (EI/DI) m/z: 651 (M+−98).

| ¹H—NMR (CDCl₃) δ ppm: | |
|---|---|
| 0.5–2.5 | (CH, CH₂ and CH₃) |
| 2.63 | (2H, J = 6.0Hz, —NCH₂CH₂S—) |
| 3.17 | (2H, d, J = 8.0Hz, —SCH₂CH=) |
| 3.48 | (2H, m, —NCH₂CH₂S—) |
| 3.67 | (1H, m, C₃—H) |
| 4.20 | (3H, m, —CH=C— × 3) |
| 6.31 | (3H, m, vinyl-H and NH) |
| 9.10 | (1H, s, COOH) |

EXAMPLE 2

11-Deoxoglycyrrhetic acid 3-hemiester derivatives (Compounds 3b–3i) listed in following Table 5 were prepared with use of the corresponding 3β-hydroxy-18β-olean-12-en-30-amides (2b–2l), by the similar procedure as in the case of Example 1.

2b–2i

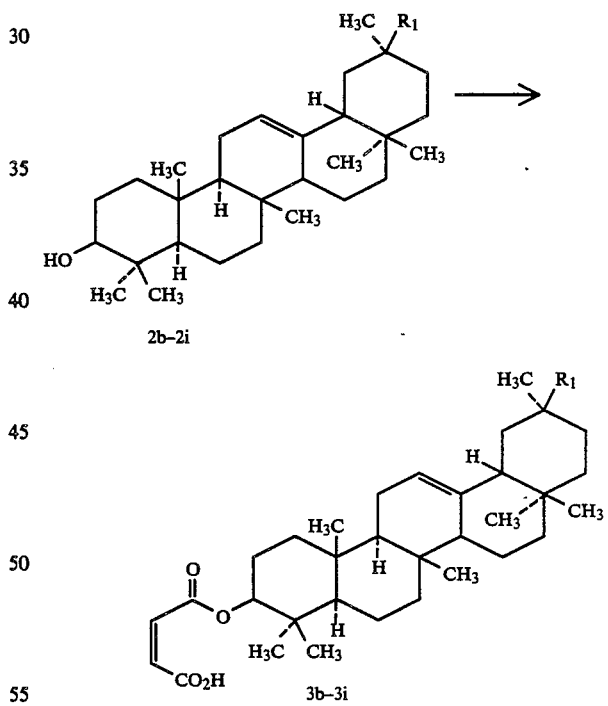

3b–3i

TABLE 5

| Compd. | R₁ | Yield (%) | m.p. (°C.) | MS(EI/DI) (m/z) |
|---|---|---|---|---|
| 3b | CONH-CH₂CH₂-S-(CH₂-CH=C(CH₃)-CH₂)₃-H | 74.1 | 75–80 | 720 (M-98) 81 (base peak) |
| 3c | CONH-CH₂CH₂-S-(CH₂-CH=C(CH₃)-CH₂)₄-H | 61.2 | amorphous | 787 (M-98) 189 (base peak) |

TABLE 5-continued

| Compd. | R₁ | Yield (%) | m.p. (°C.) | MS(EI/DI) (m/z) |
|---|---|---|---|---|
| 3d | CONH-CH₂CH₂-S-(CH₂-C(CH₃)=CH-CH₂)₉-H | 73.8 | oil | 615<br>79 (base peak) |
| 3e | CONH-CH₂CH₂-S-(CH₂-C(CH₃)=CH-CH₂)₁₀-H | 68.7 | oil | 684<br>69 (base peak) |
| 3f | CONH-CH₂CH₂-S-CH₂-CH=C(CH₃)-(CH₂CH₂CH(CH₃)CH₂)₃-H | 62.9 | amorphous | 793 (M-98)<br>514 (base peak) |
| 3g | CON-piperazine-N-(CH₂-C(CH₃)=CH-CH₂)₃-H | 70.6 | 136–138 | 729 (M-97)<br>69 (base peak) |
| 3h | COO-(CH₂-C(CH₃)=CH-CH₂)₃-H | 56.1 | 161–164 | 437 (base peak) |
| 3i | CON-piperazine-N-(2-MeO-C₆H₄) | 77.9 | 191–193 | 611 (base peak) |

EXAMPLE 3

N-[2-(3,7,11-Trimethyl-2,6,10-dodecatrien-1-ylthio)ethyl]-3β-(3-carboxy-cis-propenoyloxy)-11-oxo-18β-olean-12-en-30-amide (Compound 3j)

A mixture of 30.9 g (31.5 mmol) of N-[2-(3,7,1-trimethyl-2,6,10-dodecatrien-1-ylthio)ethyl]-3β-hydroxy-11-oxo-18β-olean-12-en-30-amide (Compound 2j obtained by Reference Example 7) and 20.6 g (210 mmol) of maleic anhydride was heated at 100° C. for 2 hours under argon atmosphere.

The reaction mixture was poured into 1 liter of water and extracted with ethyl ether (500 ml×2) and combined organic extracts were washed with water (1 liter×3). dried over sodium sulfate and concentrated in vacuo. The resulting residue was chromatographed on silica gel and eluted with chloroform-methanol (20:1) to give 13.7 g (78.7%) of the desired compound (3j).

Melting point: 75°–80° C.

IR ($\nu_{max}^{KBr}$) cm⁻¹: 1720 (COOH), 1650 (C=O, CONH)

¹H—NMR (CDCl₃) δ ppm:
- 0.5–2.3 (60H, m, CH, CH₂ and CH₃)
- 2.39 (1H, s, C₉—H)
- 2.5–3.0 (3H, m —NCH₂CH₂S— and C₁₈—H)
- 3.21 (2H, d, J = 8.0Hz, —SCH₂CH=)
- 3.3–3.7 (2H, m, —NCH₂CH₂S—)
- 4.5–5.0 (1H, m, C₃—H)
- 5.0–5.5 (3H, m, —CH=C— × 3)
- 5.83 (1H, s, C₁₂—H)
- 6.23 (1H, br., CONH)
- 6.46 (2H, s, H-C=C-H)

MS (EI/DI) m/z: 734 (M⁺—98), 530 (base peak).

EXAMPLE 4

Glycyrrhetic acid 3-hemiester derivatives (Compounds 3k and 3l) listed in following Table 6 were prepared with use of the corresponding 3β-hydroxy-11-oxo-18β-olean-12-en-30-amides (2k and 2l), by the similar procedure as in the case of Example 3.

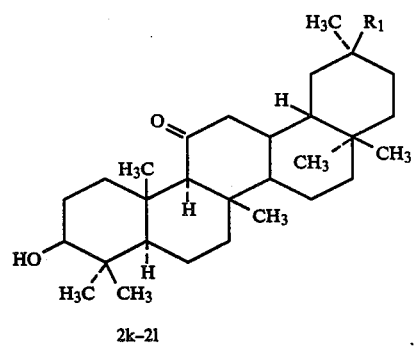

2k–2l

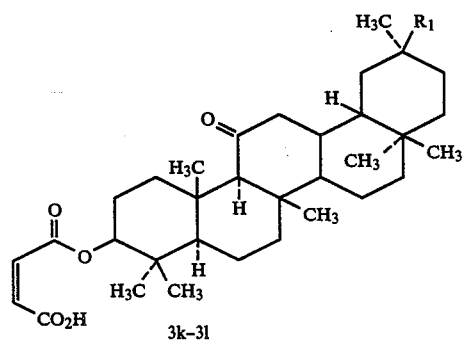

3k–3l

TABLE 6

| Compd. | R₁ | Yield % | m.p. (°C.) | MS(EI/DI) (m/z) |
|---|---|---|---|---|
| 3k | CONH~~~S-(CH=CH)₁₀-H (with methyl branch) | 75.3 | oil | 81 (base peak) |
| 3l | CON-piperazine-N-(o-methoxyphenyl) | 69.0 | 168–171 | 742 (M+)<br>149 (base peak) |

EXAMPLE 5

1-[3β-(β-Carboxypropenoyl)-18β-olean-12-en-30-oyl]-4-(o-methoxyphenyl)piperazine (Compound 3m)

A mixture of 7.00 g (11.1 mmol) of 1-(3β-hydroxy-18β-olean-12-en-30-oyl)-4-(o-methoxyphenyl)piperazine (Compound 2i obtained by Reference Example 6) and 70.0 g (0.0700 mol) of succinic anhydride was heated at 140° C. under argon atmosphere and stirred for 1 hour.

The reaction mixture was poured into about 1 liter of water to obtain a precipitate. The precipitate was washed with water, dissolved in 500 ml of ethyl ether and the organic layer was dried over sodium sulfate and concentrated in vacuo. The resulting residue was chromatographed on silica gel and eluted with ethyl ether to give 6.20 g (76.4%) of the desired compound (3m).

Melting point: 198°–200° C.

Elementary analysis: $C_{45}H_{66}N_2O_6 \cdot \frac{1}{2}H_2O$, Calc.: C, 73.04; H, 9.13; N, 3.78, Found: C, 72.98; H, 9.59; N, 3.76.

IR $(\nu_{max}^{KBr})$ cm$^{-1}$: 3440, 3000–2500 (OH), 1730 (COOH), 1710 (—COO—), 1630 (CONH), 1600, 1505 (aromatic ring).

$^1$H—NMR (CDCl₃) δ ppm:
 0.82 (3H, s, CH₃)
 0.88 (6H, s, CH₃ × 2)
 0.97 (6H, s, CH₃ × 2)
 1.15 (3H, s, CH₃)
 1.23 (3H, s, CH₃)
 2.63 (4H, brs. HOOCCH₂CH₂CO—)
 3.07 (4H, m, —CH₂–N—Ph / —CH₂—)
 3.87 (4H, m, CON(CH₂—/CH₂—))
 3.87 (3H, s, Ph—OCH₃)
 4.53 (4H, m, C₃—H)
 5.33 (1H, m, C₁₂—H)
 6.93 (4H, m, Ar—H)
 10.25 (1H, brs. COOH)

MS (EI/DI) m/z: 730 (M+), 630 (M+ −100), 612 (base peak)

EXAMPLE 6

N-[2-(3,7-Dimethyl-2,6-octadien-1-ylthio)ethyl]-3β-(3-carboxy-cis-propenoyloxy)-18β-olean-12-en-30-amide sodium salt (Compound 4a)

To a solution of 6.50 g (8.68 mmol) of N-[2-(3,7-Dimethyl-2,6-octadien-1-ylthio)ethyl]-3β-(3-carboxy-cis-propenoyloxy)-18β-olean-12-en-30-amide (Compound 3a obtained by Example 1) in 200 ml of ethanol was added aqueous solution (100 ml) containing 0.46 g (4.34 mmol) of sodium carbonate and the mixture was stirred at 20° C. for 30 minutes.

The reaction mixture was concentrated in vacuo and the resulting precipitate was filtered, washed with ethyl ether and dried to give 6.10 g (91.0%) of the desired compound (4a).

Melting point: 137.5° C.

Elementary analysis: $C_{46}H_{70}NO_5SNa \cdot 3/2H_2O$, Cal.: C, 69.14; H, 9.21; N, 1.75, Found: C, 69.30; H, 9.12; N, 1.79.

IR $(\nu_{max}^{KBr})$ cm$^{-1}$: 1715, 1645 (C=O).

$^1$H—NMR (CDCl₃) δppm:
 0.50–2.50 (CH, CH₂, CH₃)
 2.63 (2H, t, J = 8.0Hz, —NCH₂CH₂S—)
 3.35 (2H, d, J = 8.0Hz, —SCH₂CH=)
 3.53 (2H, m, —NCH₂CH₂S—)
 4.81 (1H, m, C₃—H)
 5.45 (3H, m, —CH=C × 3)

5.94, 6.75 (2H, each d, J = 12Hz, H–C=C–H )

EXAMPLE 7

Sodium salts of 11-deoxoglycyrrhetinic acid 3-hemiester derivatives (Compounds 3b–3i) listed in following Table 7 were prepared with use of the corresponding 11-deoxyglycyrrhetinic acid 3-hemiester derivatives (3b–3i), by the similar procedure as in the case of Example 6.

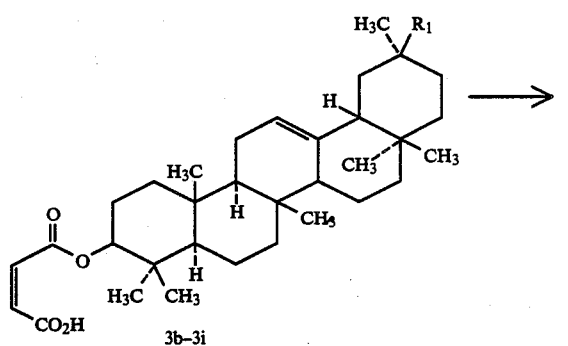

EXAMPLE 8

N-[2-(3,7,11-Trimethyl-2,6,10-dodecatrien-1-ylthio)ethyl]-3β-(3-carboxy-cis-propenoyloxy)-11-oxo-18β-olean-12-en-30-amide sodium salt (Compound 4j)

To a solution of 13.0 g (15.6 mmol) of N-[2-(3,7,11-Trimethyl-2,6,10-dodecatrien-1-ylthio)ethyl]-3β-(3-carboxy-cis-propenoyloxy)-11-oxo-18β-olean-12-en-30-amide (Compound 3j obtained by Example 3) in 130 ml of ethanol was added an aqueous solution (130 ml) containing 828 mg (7.81 mmol) of sodium carbonate and the mixture was stirred at 20° C. for 30 minutes.

The reaction mixture was concentrated in vacuo and the resulting precipitate was filtered, washed with n-hexane and dried to give 6.10 g (92.0%) of the desired compound (4j).

Melting point: 145°–147° C.

Elementary analysis: $C_{51}H_{77}NO_6SNa \cdot H_2O$, Cal.: C, 70.23; H, 9.01; N, 1.61, Found: C, 70.37; H, 9.05; N, 1.60.

IR $(\nu_{max}^{KBr})$ cm$^{-1}$: 1710 (ester), 1650 (C=O, CONH), 1580 (COO$^-$).

| $^1$H—NMR (CDCl$_3$ + CD$_3$OD = 2:1) δ ppm: | |
|---|---|
| 0.5–2.3 | (62H, m, CH, CH$_2$, CH$_3$) |
| 2.44 | (1H, s, C$_9$—H) |
| 2.5–3.1 | (3H, m, —NCH$_2$CH$_2$S—, C$_{18}$—H) |
| 3.24 | (2H, d, J=8.0Hz, —SCH$_2$CH=) |
| 3.2–3.8 | (2H, m, —NCH$_2$CH$_2$S—) |
| 4.4–4.8 | (1H, m, C$_3$—H) |

TABLE 7

| Compd. | R$_1$ | Yield (%) | m.p. (°C.) |
|---|---|---|---|
| 4b | CONH—CH$_2$CH$_2$—S—(CH$_2$CH=C(CH$_3$)CH$_2$)$_3$—H | 97.0 | 133–136 |
| 4c | CONH—CH$_2$CH$_2$—S—(CH$_2$CH=C(CH$_3$)CH$_2$)$_4$—H | 91.2 | 118–124 |
| 4d | CONH—CH$_2$CH$_2$—S—(CH$_2$CH=C(CH$_3$)CH$_2$)$_9$—H | 89.7 | amorphous |
| 4e | CONH—CH$_2$CH$_2$—S—(CH$_2$CH=C(CH$_3$)CH$_2$)$_{10}$—H | 96.6 | amorphous |
| 4f | CONH—CH$_2$CH$_2$—S—CH$_2$CH=C(CH$_3$)(CH$_2$CH$_2$CH(CH$_3$)CH$_2$)$_3$—H | 92.0 | 100–105 |
| 4g | CON(azetidinyl)—(CH$_2$CH=C(CH$_3$)CH$_2$)$_3$—H | 88.6 | 136–139 |
| 4h | COO—(CH$_2$CH=C(CH$_3$)CH$_2$)$_3$—H | 92.1 | 115–117 |
| 4i | CON(azetidinyl)-phenyl-OMe | 95.4 | 207–210 |

-continued

| ¹H—NMR (CDCl₃ + CD₃OD = 2:1) δ ppm: | |
|---|---|
| 5.0–5.5 | (3H, m, —CH=C × 3) |
| 5.79 | (1H, s, C₁₂—H) |
| 5.80, 6.64 | (2H, each d, J=12Hz,  ) |

EXAMPLE 9

Sodium salts of glycyrrhetinic acid 3-hemiester derivatives (Compounds 4k and 4l) listed in following Table 8 were prepared with use of the corresponding 11-deoxyglycyrrhetinic acid 3-hemiester derivatives (3k and 3l), by the similar procedure as in the case of Example 8.

-continued

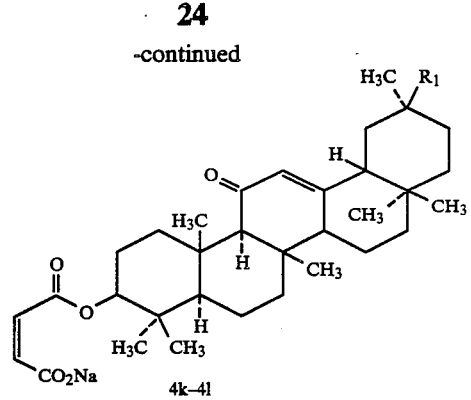

4k-4l

TABLE 8

| Compd. | R₁ | Yield (%) | m.p. (°C.) |
|---|---|---|---|
| 4k | CONH~~~S(~~~=~~~)₁₀H | 97.4 | amorphous |
| 4l | CON-N-(o-MeO-C₆H₄) | 82.7 | 192–196 |

Elementary Analysis

The data of elementary analysis for Compounds 4b, 4c, 4d, 4e, 4f, 4g, 4h, 4i, 4k and 4l are listed in following Table 9.

TABLE 9

| Compd. | Formula | Calculated (%) C | H | N | Found (%) C | H | N |
|---|---|---|---|---|---|---|---|
| 4b | C₅₁H₇₈NNaO₅S.3/2H₂O | 70.63 | 9.41 | 1.62 | 70.49 | 9.42 | 1.58 |
| 4c | C₅₆H₈₆NNaO₅S.2/3H₂O | 73.08 | 9.57 | 1.52 | 72.86 | 9.97 | 1.42 |
| 4d | C₈₁H₁₂₆NNaO₅S.H₂O | 76.79 | 10.18 | 1.11 | 76.86 | 10.96 | 1.09 |
| 4e | C₈₆H₁₃₄NNaO₅S.H₂O | 77.40 | 10.27 | 1.05 | 77.32 | 10.97 | 1.07 |
| 4f | C₅₆H₉₂NNaO₅S.H₂O | 72.13 | 9.95 | 1.50 | 71.81 | 10.27 | 1.46 |
| 4g | C₅₃H₈₁N₂NaO₅.H₂O | 73.40 | 9.65 | 3.23 | 73.44 | 9.82 | 3.23 |
| 4h | C₄₉H₇₃NaO₆.1/2H₂O | 74.49 | 9.44 | — | 74.16 | 9.64 | — |
| 4i | C₄₅H₆₃N₂NaO₆.H₂O | 70.28 | 8.52 | 3.64 | 69.91 | 8.62 | 3.60 |
| 4k | C₈₆H₁₃₂NNaO₆S.H₂O | 76.57 | 10.01 | 1.04 | 76.33 | 10.30 | 1.10 |
| 4l | C₄₅H₆₁N₂NaO₇.H₂O | 69.03 | 8.11 | 3.58 | 68.81 | 8.16 | 3.62 |

EXAMPLE 10

1-[3β-(β-carboxypropenoyloxy)-18β-olean-12-en-30-oyl]-4-(o-methoxyphenyl)piperazine sodium salt (Compound 4m)

To a solution of 5.60 g (7.67 mmol) of 1-[3β-(β-carboxypropenoyloxy)-18β-olean-12-en-30-oyl]-4-(o-methoxyphenyl)piperazine (Compound 3m obtained by Example 3) in 150 ml of ethanol was added an aqueous solution (20 ml) containing 828 mg (7.81 mmol) of sodium carbonate and the mixture was stirred at 20° C. for 30 minutes.

The reaction mixture was concentrated in vacuo. The resulting residue was crystalized with ethyl ether, filtered and dried to give 5.30 g (91.9%) of the desired compound (4m).

Melting point: 211°–215° C. (dec.).

Elementary analysis: C₄₅H₆₅NaN₂O₆.H₂O. Cal.: C, 70.10; H, 8.97; N, 3.72, Found: C, 69.87; H, 9.22; N, 3.67.

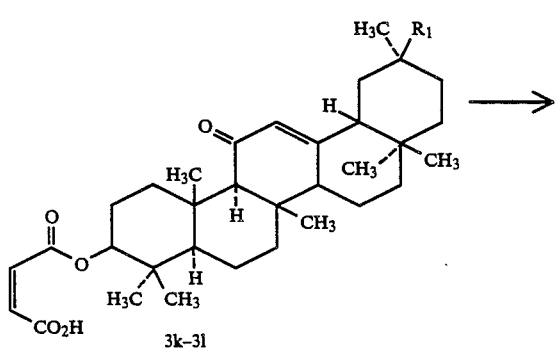

3k-3l

IR ($\nu_{max}^{KBr}$) cm$^{-1}$: 3440 (OH), 1725 (ester), 1630 (CONH), 1580 (COO$^-$), 1500 (aromatic ring).

| $^1$H—NMR (CDCl$_3$ + CD$_3$OD = 1:2) δppm: | |
|---|---|
| 0.82 | (3H, s, CH$_3$) |
| 0.90 | (6H, s, CH$_3$ × 2) |
| 0.98 | (6H, s, CH$_3$ × 2) |
| 1.17 | (3H, s, CH$_3$) |
| 1.25 | (3H, s, CH$_3$) |
| 2.87 | (4H, brs., HOOCCH$_2$CH$_2$CO—) |
| 3.10 | (4H, m, —CH$_2$\N—Ph / —CH$_2$) |
| 3.87 | (4H, m, —CON\ CH$_2$— / CH$_2$—) |
| 3.90 | (3H, m, Ph—OCH$_3$) |
| 4.50 | (1H, m, C$_3$—H) |
| 5.35 | (1H, m, C$_{12}$—H) |
| 6.95 | (4H, m, Ar—H) |

EXAMPLE 11

Methyl 3β-(β-carboethoxymethoxy)-18β-olean-12-en-30-oate (Compound 5)

To a mixture of 13.0 g (27.7 mmol) of methyl 3β-hydroxy-18β-olean-12-en-30-oate and 30 mg (0.068 mmol) of rhodium (II) acetate dimer in 400 ml of methylene chloride was added dropwise a solution of 5.00 g (43.9 mmol) of ethyl diazoacetate in 50 ml of methylene chloride with stirring at 25° C. for 1.5 hours under argon atmosphere.

The reaction mixture was washed with water, dried over sodium sulfate and concentrated in vacuo. The resulting residue was crystalized with methanol, filtered and dried to give 13.5 g (88.2%) of the desired compound (5).

Melting point: 155°–156° C.

IR ($\nu_{max}^{KBr}$) cm$^{-1}$: 1760 (COOEt), 1725 (COOMe), 1630 (C=C),

MS (EI/DI) m/z: 556 (M+), 262 (base peak)

| $^1$H—NMR (CDCl$_3$) δ ppm: | |
|---|---|
| 0.78 | (3H, s, CH$_3$) |
| 0.83 | (3H, s, CH$_3$) |
| 0.97 | (6H, s, CH$_3$ × 2) |
| 1.05 | (3H, s, CH$_3$) |
| 1.12 | (6H, s, CH$_3$ × 2) |
| 1.28 | (3H, t, J = 7.0 Hz, —COOCH$_2$CH$_3$) |
| 1.0–2.1 | (23H, m, CH, CH$_2$) |
| 2.90 | (1H, m, C$_3$—H) |
| 3.67 | (3H, s, —COOCH$_3$) |
| 4.10 | (2H, s, —OCH$_2$COOC$_2$H$_5$) |
| 4.20 | (2H, q, J = 7.0 Hz, —COOCH$_2$CH$_3$) |
| 5.27 | (1H, m, C$_{12}$—H) |

EXAMPLE 12

3β-(carboxymethoxy)-18β-olean-12-en-30-oic acid disodium salt (Compound 6)

To a suspension of 11.3 g (20.3 mmol) of methyl 3β-(carboethoxymethoxy)-18β-olean-12-en-30-oate (Compound 5 obtained by Example 11) in 140 ml of dimethyl sulfoxide was added a 20% aqueous solution of 28.5 g (102 mmol) of potassium hydroxide and the mixture was refluxed for 30 minutes under argon atmosphere.

The reaction mixture was cooled, poured into ice water, acidified with concentrated hydrochloric acid and then extracted with ethyl acetate (1.5 liter). The organic extract was washed with water (1 liter×3), dried over sodium sulfate and concentrated in vacuo. The resulting residue was recrystalized from methanol to give 8.32 g (79.6%) of 3β-(carboxymethoxy)-18β-olean-12-en-30-oic acid. To a solution of 6.13 g (11.9 mmol) of this acid in methanol-methylene chloride (2:1) was added aqueous solution of 1.27 g (11.9 mmol) of sodium carbonate and the mixture was stirred at 20° C. for 15 minutes. The reaction mixture was evaporated in vacuo. The resulting residue was crystalized with acetone, filtered and dried to give 6.65 g (100%) of the desired compound (6).

Melting point: 310°–312° C. (dec.)

Elementary analysis: C$_{32}$H$_{48}$Na$_2$O$_5$.3/2H$_2$O. Cal.: C, 65.62; H, 8.78, Found: C, 65.38; H, 9.11.

IR ($\nu_{max}^{KBr}$) cm$^{-1}$: 3430 (OH), 1600, 1550 (COO$^-$).

| $^1$H—NMR (CD$_3$OD) δ ppm: | |
|---|---|
| 0.80 | (3H, s, CH$_3$) |
| 0.88 | (3H, s, CH$_3$) |
| 1.00 | (6H, s, CH$_3$× 2) |
| 1.07 | (6H, s, CH$_3$× 2) |
| 1.18 | (3H, s, CH$_3$) |
| 1.0–2.1 | (23H, m, CH, CH$_2$) |
| 2.86 | (1H, m, C$_3$—H) |
| 3.93 | (2H, s, —OOCCH$_2$O—) |
| 5.35 | (1H, m, C$_{12}$—H) |

EXAMPLE 13

3β-(2-Cyanoethoxy)-18β-olean-12-en-30-oic acid (Compound 7)

To a solution of 25.0 g (54.8 mmol) of 3β-hydroxy-18β-olean-12-en-30-oic acid in 500 ml of tetrahydrofuran was added 1.58 g (65.8 mmol) of sodium hydroxide with cooling on ice bath. After stirring for 10 minutes, 8.73 g (164 mmol) of acrylonitrile were added and the mixture was refluxed for 2 hours under argon atmosphere.

The reaction mixture was cooled, poured into ice water, acidified with concentrated hydrochloric acid and then the resulting precipitate was filtered and washed with water.

The resulting crude product was chromatographed on silica gel and eluted with methylene chloride to give 12.6 g (40.0%) of the desired compound (7).

IR ($\nu_{max}^{KBr}$) cm$^{-1}$: 3000–2500 (OH), 2250 (C≡N), 1700 (COOH), 1630 (C=C).

| $^1$H—NMR (CDCl$_3$) δ ppm: | |
|---|---|
| 0.80 | (6H, s, CH$_3$ × 2) |
| 0.97 | (6H, s, CH$_3$ × 2) |
| 1.00 | (3H, s, CH$_3$) |
| 1.15 | (3H, s, CH$_3$) |
| 1.22 | (3H, s, CH$_3$) |
| 1.0–2.1 | (23H, m, CH, CH$_2$) |
| 2.60 | (2H, m, —OCH$_2$CH$_2$CN) |
| 2.87 | (1H, m, C$_3$—H) |
| 3.77 | (2H, s, —CH$_2$CN) |
| 5.30 | (1H, m, C$_{12}$—H) |

MS (EI/DI) m/z: 509 (M+), 248 (base peak).

EXAMPLE 14

3β-(2-Carbamoylethoxy)-18β-olean-12-en-30-oic acid (Compound 8)

To a suspension of 15.8 g (31.0 mmol) of 3β-(2-cyanoethoxy)-18β-olean-12-en-30-oic acid (Compound 7 obtained by Example 13) in 600 ml of 1,4-dioxane was added 118 ml (600 mmol) of 20% aqueous solution of potassium hydroxide and then added dropwise 400 ml (3.50 mol) of 30% hydrogen peroxide over a period of 6 hours at 45°–50° C. with stirring.

The reaction mixture was poured into ice water, acidified with concentrated hydrochloric acid and then extracted with ethyl acetate (1.5 liter). The organic extract was washed with an aqueous solution of sodium bisulfite and water, dried over sodium sulfate, and evaporated in vacuo.

The resulting crude product was chromatographed on silica gel and eluted with methylene chloride to give 9.38 g (57.2%) of the desired compound (8).

Melting point: 290°–291° C. (dec.).

IR $(\nu_{max}^{KBr})$ cm$^{-1}$: 3440, 3000–2500 (OH), 3350, 3220 (NH$_2$), 1725 (COOH), 1700 (CONH), 1655 (NH$_2$).

| $^1$H—NMR (CDCl$_3$ + CD$_3$OD = 3:1) δ ppm: | |
|---|---|
| 0.80 | (6H, s, CH$_3$ × 2) |
| 0.98 | (9H, s, CH$_3$ × 3) |
| 1.17 | (6H, s, CH$_3$ × 2) |
| 1.0–2.1 | (23H, m, CH, CH$_2$) |
| 2.48 | (2H, t, J = 6.0 Hz, —OCH$_2$CH$_2$CON—) |
| 2.86 | (1H, m, C$_3$—H) |
| 3.73 | (2H, s, —CH$_2$CON—) |
| 5.30 | (1H, m, C$_{12}$—H) |

MS (EI/DI) m/z: 527 (M+), 248 (base peak).

EXAMPLE 15

3β-(2-Carboxyethoxy)-18β-olean-12-en-30-oic acid disodium salt (Compound 9)

To a suspension of 2.50 g (4.74 mmol) of 3β-(2-carbamoylethoxy)-18β-olean-12-en-30-oic acid (Compound 8 obtained by Example 14) in 50 ml of acetic acid was added 10.0 ml (95.9 mmol) of concentrated hydrochloric acid and the mixture was refluxed for 1 hour.

The reaction mixture was cooled, poured into ice water, and the resulting precipitate was filtered and washed with water.

The resulting crude product was chromatographed on silica gel and eluted with methylene chloride-ethyl ether (9:1) to give 2.10 g (84.0%) of 3β-(2-carboxyethoxy)-18β-olean-12-en-30-oic acid.

To a solution of 2.10 g (3.98 mmol) of this acid in methanol-methylene chloride (5:1) was added an aqueous solution of 422 mg (3.98 mmol) of sodium carbonate and the mixture was stirred at 20° C. for 20 minutes. The reaction mixture was evaporated in vacuo. The resulting residue was crystalized with acetone, filtered and dried to give 2.30 g (100%) of the desired compound (9).

Melting point: 295°–300° C. (dec.).

IR $(\nu_{max}^{KBr})$ cm$^{-1}$: 1565, 1400 (COO).

| $^1$H—NMR (CD$_3$OD) δ ppm: | |
|---|---|
| 0.80 | (6H, s, CH$_3$ × 2) |

| $^1$H—NMR (CD$_3$OD) δ ppm: -continued | |
|---|---|
| 1.00 | (9H, s, CH$_3$ × 3) |
| 1.07 | (3H, s, CH$_3$) |
| 1.20 | (3H, s, CH$_3$) |
| 1.0–2.1 | (23H, m, CH, CH$_2$) |
| 2.47 | (2H, t, J = 6.0 Hz, —OCH$_2$CH$_2$COO—) |
| 2.70 | (1H, m, C$_3$—H) |
| 3.70 | (2H, s, —CH$_2$COO—) |
| 5.37 | (1H, m, C$_{12}$—H) |

MS (EI/DI) m/z: 527 (M+), 248 (base peak).

Pharmacological Test Example 1

(Action to stress ulcer in rats)

Male Wister rats weighing about 180 g (age: 6 weeks) were used for this experiment.

Ten rats in each group were deprived of food for 24 hours before the experiment. They were immobilized in a restraint cage and immersed for 7 hours to the height of the xiphoid in a water bath kept at 23±1° C. After inflation with 10 ml of 1% formalin, the isolated stomach was opened along the greater curvature. The ulcer index (UI) was determined as the sum of the length (mm) of each erosion per rat. Each of the compounds to be tested was suspended in 5% gum arabic solution and given orally 30 minutes before restraint. Control animals received the same solution without any drug or the test compound.

Inhibition ratio is expressed as follows.

$$\text{Inhibition ratio (\%)} = \frac{UI \text{ (control)} - UI \text{ (test)}}{UI \text{ (control)}} \times 100$$

Results are shown in following Table 10.

TABLE 10

| Compound | Dosage (mg/kg, po) | Ulcer Index (%) |
|---|---|---|
| 4a | 25 | 21.1 |
|  | 50 | 58.2 |
|  | 100 | 73.1 |
| 4b | 25 | 51.0 |
|  | 50 | 62.6 |
|  | 100 | 60.5 |
| 4c | 12.5 | 33.3 |
|  | 25 | 30.5 |
|  | 50 | 46.8 |
|  | 100 | 61.0 |
| 4d | 12.5 | 33.9 |
|  | 25 | 55.4 |
|  | 50 | 42.1 |
|  | 100 | 56.2 |
| 4e | 12.5 | 50.0 |
|  | 25 | 44.7 |
|  | 50 | 53.5 |
|  | 100 | 60.5 |
| 4f | 25 | 16.5 |
|  | 50 | 4.3 |
|  | 100 | 34.5 |
| 4g | 12.5 | 11.7 |
|  | 25 | 22.5 |
|  | 50 | 21.6 |
| 4h | 12.5 | 8.0 |
|  | 25 | 6.1 |
|  | 50 | 35.7 |
| 2i | 25 | −18.0 |
|  | 50 | 4.9 |
|  | 100 | 46.4 |
| 4i | 25 | 24.4 |
|  | 50 | 61.4 |
|  | 100 | 76.5 |
| 4k | 12.5 | 48.5 |
|  | 25 | 45.5 |
|  | 50 | 43.6 |
|  | 100 | 56.4 |

TABLE 10-continued

| Compound | Dosage (mg/kg, po) | Ulcer Index (%) |
| --- | --- | --- |
| 4l | 12.5 | 6.3 |
|  | 25 | 25.9 |
|  | 50 | 31.7 |
| 4m | 25 | 9.5 |
|  | 50 | 26.5 |
|  | 100 | 23.2 |
| 6 | 25 | 7.2 |
|  | 50 | 42.5 |
|  | 100 | 59.8 |
| 9 | 25 | −0.7 |
|  | 50 | 11.8 |
|  | 100 | 26.1 |

Pharmacological Test Example 2

(Action to gastric necrosis in rats)

Male Sprague-Dewley rats weighing about 250 g were used for this experiment.

Ten rats in each group were deprived of food for 24 hours before the experiment. Each of the compounds to be tested was suspended in 5% gum arabic solution and given orally to the test animal. After 1 hours from the administration of the compound. 1 ml of absolute ethanol was administered orally and the animals were killed 1 hour later from the ethanol administration. After inflation with 10 ml of 1% formalin, the isolated stomach was opened along the greater curvature. The ulcer index (UI) was determined as the sum of the length (mm) of each erosion per rat. 30 minutes before restraint. Control animals received the same solution without any drug or the test compound.

Inhibition ratio is expressed as follows.

$$\text{Inhibition ratio (\%)} = \frac{UI \text{ (control)} - UI \text{ (test)}}{UI \text{ (control)}} \times 100$$

Results are shown in following Table II.

TABLE 11

| Compound | Dosage (mg/kg, po) | Ulcer Index (%) |
| --- | --- | --- |
| 4c | 25 | 43.3 |
|  | 50 | 66.1 |
|  | 100 | 48.9 |
| 4d | 25 | 31.7 |
|  | 50 | 20.6 |
|  | 100 | 39.2 |
| 4e | 25 | 21.3 |
|  | 50 | −9.5 |
|  | 100 | −34.7 |
| 4k | 25 | 58.7 |
|  | 50 | 10.9 |
|  | 100 | 14.3 |

Pharmaceutical Test Example 3

(Acute toxicity)

Male ICR strain mice weighing 24 to 30 g were used for this experiment. The animals were classified into groups, each of 5 mice. Each of the compounds to be tested was suspended in 2% Tween 80 solution and given orally. General condition, behavior, body weight and mortality were observed daily throughout the experimental period of 7 days.

Results are shown in following Table 12.

TABLE 12

| Compound | LD$_{50}$ (mg/kg) |
| --- | --- |
| 4c | 1000 |

TABLE 12-continued

| Compound | LD$_{50}$ (mg/kg) |
| --- | --- |
| 4d | 1000 |
| 4e | 1000 |
| 4k | 1000 |

Prescriptional Example 1 (Capsule)

Following ingredients were composed and treated in a conventional manner to prepare capsules.

| Compound 4b | 20 (mg) |
| --- | --- |
| Lactose | 50 |
| Potato starch | 50 |
| Crystalline cellulose | 109 |
| Magnesium stearate | 1 |
|  | 230 mg/capsule |

Prescriptional Example 2 (Tablet)

Following ingredients were composed and treated in a conventional manner to prepare tablets.

| Compound 4e | 20 (mg) |
| --- | --- |
| Crystalline cellulose | 20 |
| Lactose | 41 |
| Corn starch | 30 |
| Hydroxypropylcellulose | 6 |
| Magnesium stearate | 3 |
|  | 120 mg/tablet |

Prescriptional Example 3 (Granule)

Following ingredients were composed and treated in a conventional manner to prepare granules.

| Compound 4k | 20 (mg) |
| --- | --- |
| Lactose | 550 |
| Corn starch | 330 |
| Hydroxypropylcellulose | 20 |
|  | 920 mg/package |

What is claimed is:

1. A glycyrrhetic acid derivative of the formula

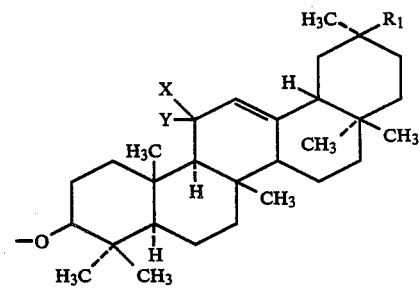

wherein X and Y are hydrogen atom, respectively or X is oxygen atom together with Y, A$_1$ is methylene or carbonyl radical, A$_2$ is hydrogen atom, cyano, carbamoyl, carboxy radical or alkoxycarbonyl group, m and n are an integer, respectively, R$_1$ is a radical of —COOR$_2$  (Ia)

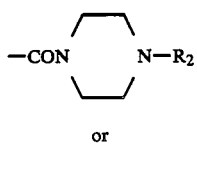 (Ib)

or

—CONH—(CH$_2$)$_l$—A$_3$—R$_2$ (Ic)

in which R$_2$ is an alkyl, alkenyl group, phenyl radical or a substituted phenyl radical, A$_3$ is S, O or NH, and l is an integer, and a salt thereof.

2. The derivative as set forth in claim 1, wherein said derivative is 3β-(carboxymethoxy)-18β-olean-12-en-oic acid.

3. The derivative as set forth in claim 1, wherein said derivative is 3β-(2-carboxyethoxy)-18β-olean-12-en-30-30-oic acid.

4. The derivative as set forth in claim 1, wherein said derivative is N-[2-(3,7-dimethyl-2,6-octadien-1-ylthio)ethyl]-3β-(3-carboxy-cispropenoyloxy)-18β-olean-12-en-30-amide.

5. The derivative as set forth in claim 1, wherein said derivative is N-[2-(3,7,11-trimethyl-2,6,10-dodecatrien-1-ylthio)ethyl]-3β-(3-carboxy-cis-propenoyloxy)-18β-olean-12-en-30-amide.

6. The derivative as set forth in claim 1, wherein said derivative is N-[2-(3,7,11,14-tetramethyl-2,6,10,14-hexadecatrien-1-ylthio)ethyl]-3β-(3-carboxy-cis-propenoyloxy)-18β-olean-12-en-30-amide.

7. The derivative as set forth in claim 1, wherein said derivative is N-[2-(3,7,11,15,19,23,27,31,35-nonamethyl-2,6,10,14,18,22,26,30,34-hexatriacontanonaen-1-ylthio)ethyl]-3β-(3-carboxy-cis-propenoyloxy)-18β-olean-12-en-30-amide.

8. The derivative as set forth in claim 1, wherein said derivative is N-[2-(3,7,11,15,19,23,27,31,35,39-decamethyl-2,6,10,14,18,22,26,30,34,38-tetracontadecaen-1-ylthio)ethyl]-3β-(3-carboxy-cis-propenoyloxy)-18β-olean-12-en-30-amide.

9. The derivative as set forth in claim 1, wherein said derivative is N-[2-(3,7,11,15-tetramethyl-2-hexadecaen-1-ylthio)ethyl]-3β-(3-carboxy-cis-propenoyloxy)-18β-olean-12-en-30-amide.

10. The derivative as set forth in claim 1, wherein said derivative is N-[2-(3,7,11-trimethyl-2,6,10-dodecatrien-1-ylthio)ethyl]-3β-(3-carboxy-cis-propenoyloxy)-11-oxo-18β-olean-12-en-30-amide.

11. The derivative as set forth in claim 1, wherein said derivative is N-[2-(3,7,11,15,19,23,27,31,35,39-decamethyl-2,6,10,14,18,22,26,30,34,38-tetracontadecaen-1-ylthio)ethyl]-3β-(3-carboxy-cis-propenoyloxy)-11-oxo-18β-olean-12-en-30-amide.

12. The derivative as set forth in claim 1, wherein said derivative is 1-[3β-(3-carboxy-cis-propenoyloxy)-18β-olean-12-en-30-oyl]-4-(3,7,11-trimethyl-2,6,10-dodecatrien-1-yl)piperazine.

13. The derivative as set forth in claim 1, wherein said derivative is 3,7,11-trimethyl-2,6,10-dodecatrien-1-yl 3β-(3-carboxy-cis-propenoyloxy)-18β-olean-12-en-30-oate.

14. The derivative as set forth in claim 1, wherein said derivative is 1-(3β-hydroxy-18β-olean-12-en-30-oyl)-4-(o-methoxyphenyl)piperazine.

15. The derivative as set forth in claim 1, wherein said derivative is 1-[3β-(3-carboxy-cis-propenoyloxy)-18β-olean-12-en-30-oyl]-4-(o-methoxyphenyl)piperazine.

16. The derivative as set forth in claim 1, wherein said derivative is 1-[3β-(3-carboxypropanoyloxy)-18β-olean-12-en-30-oyl]-4-(o-methoxyphenyl)piperazine.

17. The derivative as set forth in claim 1, wherein said derivative is 1-[3β-(3-carboxy-cis-propenoyloxy)-11-oxo-18β-olean-12-en-30-oyl]-4-(o-methoxyphenyl)piperazine.

18. An antiulcer composition comprising an effective amount of a glycyrrhetic acid derivative of the formula

 (I)

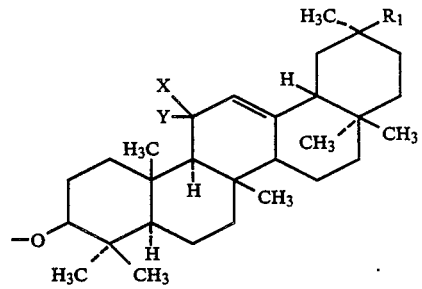

wherein X and Y are hydrogen atom, respectively or X is oxygen atom together with Y, A$_1$ is methylene or carbonyl radical, A$_2$ is hydrogen atom, cyano, carbamoyl, carboxy radical or alkoxycarbonyl group, m and n are an integer, respectively, R$_1$ is a radical of —COOR$_2$ (Ia)

 (Ib)

or

—CONH—(CH$_2$)$_l$—A$_3$—R$_2$ (Ic)

in which R$_2$ is an alkyl, alkenyl group, phenyl radical or a substituted phenyl radical, A$_3$ is S, O or NH, and l is an integer, or a pharmaceutically acceptable salt thereof, together with a pharmaceutically acceptable carrier.

* * * * *